(12) United States Patent
Yamada et al.

(10) Patent No.: US 12,096,944 B2
(45) Date of Patent: Sep. 24, 2024

(54) HEMOSTATIC DEVICE

(71) Applicant: TERUMO KABUSHIKI KAISHA, Tokyo (JP)

(72) Inventors: Tomomi Yamada, Fuji Shizuoka (JP); Yo Higashi, Fujinomiya Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 427 days.

(21) Appl. No.: 17/030,207

(22) Filed: Sep. 23, 2020

(65) Prior Publication Data

US 2021/0000481 A1 Jan. 7, 2021

Related U.S. Application Data

(63) Continuation of application No. PCT/JP2019/013315, filed on Mar. 27, 2019.

(30) Foreign Application Priority Data

Mar. 30, 2018 (JP) ................................ 2018-067413

(51) Int. Cl.
*A61B 17/135* (2006.01)
*A61B 17/12* (2006.01)

(52) U.S. Cl.
CPC ...... *A61B 17/135* (2013.01); *A61B 17/12009* (2013.01); *A61B 2017/12004* (2013.01); *A61B 2017/12018* (2013.01)

(58) Field of Classification Search
CPC .............. A61B 17/132; A61B 17/1322; A61B 17/1325; A61B 17/1327; A61B 17/135;
(Continued)

(56) References Cited

U.S. PATENT DOCUMENTS 5,512,056 A * 4/1996 Stevens .............. A61B 17/1325
606/203
5,558,095 A 9/1996 Hynson et al.
(Continued)

FOREIGN PATENT DOCUMENTS

CN 2210628 Y 10/1995
CN 2732194 Y 10/2005
(Continued)

OTHER PUBLICATIONS

Extended European Search Report mailed Apr. 1, 2021 in corresponding European Patent Application No. 19775579.6, 9 pages.
(Continued)

*Primary Examiner* — Elizabeth Houston
*Assistant Examiner* — Lindsey Bachman
(74) *Attorney, Agent, or Firm* — Kim & Stewart LLP

(57) ABSTRACT

A hemostatic device is worn on a hand having a site where bleeding is to be stopped and includes a pressing member that applies a compression force to the site. The hemostatic device further includes a cover configured to be worn on a thumb and a dorsal side of the hand, and a linear member having a first end connected to the cover and configured to secure the cover to the hand when a second end thereof is attached to the cover. The cover has a hole which surrounds a portion of the linear member and the pressing member is disposed on a distal side of the cover relative to a virtual line passing through the hole and the connection portion.

19 Claims, 6 Drawing Sheets

(58) Field of Classification Search
CPC ...... A61B 17/1355; A61B 2017/12004; A61H 39/04; A61H 2205/065
See application file for complete search history.

(56) References Cited

U.S. PATENT DOCUMENTS

| | | | |
|---|---|---|---|
| 5,667,484 A * | 9/1997 | Brossard | A61H 39/04 |
| | | | 606/201 |
| 5,695,520 A | 12/1997 | Bruckner et al. | |
| 2004/0068290 A1* | 4/2004 | Bates | A61B 17/1325 |
| | | | 606/202 |
| 2006/0190026 A1 | 8/2006 | Sanders | |
| 2012/0296369 A1 | 11/2012 | Atthoff et al. | |
| 2014/0163484 A1 | 6/2014 | Atkinson et al. | |
| 2015/0327870 A1* | 11/2015 | Fortson | A61B 17/0057 |
| | | | 606/202 |
| 2016/0120729 A1* | 5/2016 | Ankrum | A61B 17/1322 |
| | | | 601/84 |
| 2018/0042615 A1 | 2/2018 | Kimura et al. | |
| 2019/0133602 A1* | 5/2019 | Kiemeneij | A61M 39/06 |
| 2021/0145451 A1* | 5/2021 | Watanabe | A61B 17/1325 |

FOREIGN PATENT DOCUMENTS

| | | |
|---|---|---|
| CN | 201200443 Y | 3/2009 |
| CN | 203182968 U | 9/2013 |
| CN | 104994890 A | 10/2015 |
| CN | 204814040 U | 12/2015 |
| CN | 206333415 U | 7/2017 |
| JP | 2008-119517 A | 5/2008 |
| JP | 2018011798 A | 1/2018 |
| WO | 2016-163326 A1 | 10/2016 |

OTHER PUBLICATIONS

English Translation of International Search Report dated Jul. 2, 2019, mailed in counterpart International Application No. PCT/JP2019/013315, 1 page.
English Translation of Written Opinion dated Jul. 2, 2019, mailed in counterpart International Application No. PCT/JP2019/013315, 4 pages.
Office Action mailed Apr. 13, 2023 in corresponding Chinese Patent Application No. 201980010497.6, 12 pages. (with Translation).
Office Action mailed Oct. 20, 2023 in corresponding Chinese Patent Application No. 201980010497.6, 11 pages. (with Translation).

* cited by examiner

HEMOSTATIC DEVICE

CROSS-REFERENCE TO RELATED APPLICATION(S)

This application is a continuation of International Patent Application No. PCT/JP2019/013315, filed on Mar. 27, 2019, which is based upon and claims the benefit of priority from Japanese Patent Application No. 2018-067413, filed on Mar. 30, 2018, the entire contents of which are incorporated herein by reference.

FIELD

One or more embodiments disclosed herein relate to a hemostatic device.

BACKGROUND

As one of catheter procedures, a procedure of puncturing a blood vessel (for example, radial artery) of an arm of a patient to introduce various medical elongated bodies into the blood vessel via the puncture site formed in the blood vessel of the arm of the patient and performing a procedure or a treatment on a lesion site is disclosed in JP-A-2008-119517.

The radial artery extending along an arm of a human body is connected to a palmar artery. Accordingly, in recent years, a catheter procedure using distal transradial intervention (dTRI) in which the palmar artery located in the hand is punctured and treatment is performed through the puncture site, has been attempted.

The palmar artery is located in the hand and the hand has many movable portions such as fingers. Therefore, after a catheter procedure is performed in which the palmar artery is punctured, when an operator treats the puncture site located in the hand for hemostasis, it may be difficult to appropriately apply compression to the puncture site by existing hemostatic devices, which are for the arm or the leg. Therefore, a hemostatic device capable of effectively applying compression to the puncture site on the hand is desired.

When the puncture site is on the hand instead of the arm or the leg, since the hand has many movable portions such as fingers, it is difficult to properly position the hemostatic device with respect to the puncture site. The hemostatic device for supporting hemostasis on the puncture site on the hand needs to be positioned so that a pressing portion by which a compression force is applied to the puncture site is not displaced from the puncture site. In particular, when a patient opens or closes the hand, the shape of the hand is easily changed. Therefore, in the hemostatic device for supporting hemostasis on the puncture site on the hand, when the patient moves his or her hand during hemostasis, a gap may easily be formed between the pressing portion and the puncture site. Accordingly, while using the hemostatic device for supporting hemostasis on the puncture site on the hand, it is important to appropriately maintain the compression force to the puncture site even when there is movement of the hand or the like.

SUMMARY

In consideration of the above-described problems, embodiments provide a hemostatic device capable of being easily positioned with respect to a site of the hand where bleeding is to be stopped and maintaining a compression force that is applied by a pressing member to the site where the bleeding is to be stopped.

According to an embodiment, there is provided a hemostatic device including: a cover configured to be worn on a hand of a patient to cover a site on a dorsal side of the hand of the patient where bleeding is to be stopped, a pressing member configured to compress the site where the bleeding is to be stopped when the cover is worn and the pressing member is positioned on the site where the bleeding is to be stopped, and a linear member configured to secure the cover to the hand. The cover has a hole into which the linear member has been inserted, and the linear member is connected to the cover at a first end thereof and has a second end configured to be attachable to the cover. The pressing member is disposed on a distal side of the cover relative to a virtual line passing through the hole and a connection point of the first end of the linear member to the cover.

In the hemostatic device according to one or more embodiments, the pressing member is disposed in a region which is bounded by a fingertip of the thumb covered by the covering member, the hole, and the connection point of the first end of the linear member to the cover when the hemostatic device is mounted on the hand. Moreover, in the hemostatic device, a force for securing the cover to the hand acts on the hole side and the connection point side with the fingertip as a base point when the hemostatic device is mounted on the hand. Accordingly, the pressing member can be in close contact with the hand of the patient, and even when the patient moves the hand, it is possible to prevent a decrease in the compression force applied by the pressing member to the site where the bleeding is to be stopped or to prevent the pressing member from being displaced. Moreover, in the hemostatic device, the covering member is mounted on the finger of the patient. Accordingly, a predetermined range of the hand including the site where the bleeding is to be stopped with the finger as the base point is covered and the puncture site can be pressed. Therefore, the hemostatic device can be used in various patients regardless of a size of the hand which may differ from patient to patient.

DESCRIPTION OF EMBODIMENTS

Figure 1:
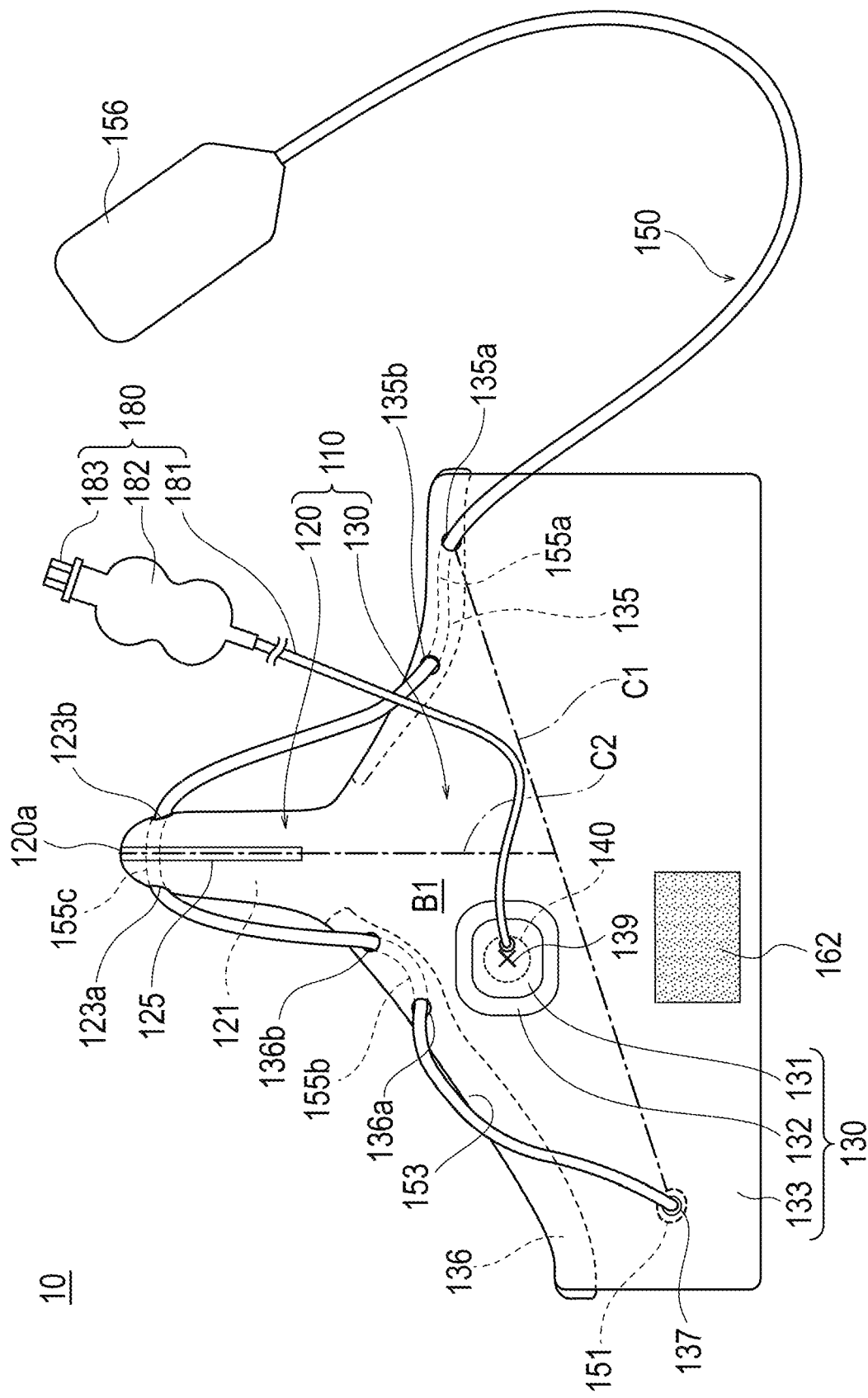
FIG. 1 is a plan view of a hemostatic device according to an embodiment as viewed from an outer surface side of the hemostatic device.

Hereinafter, one or more embodiments and modification examples thereof will be described with reference to the accompanying drawings. The following description is not intended to limit the technical scope or the definition of the terms described in the claims. In addition, dimensional ratios in the drawings may be exaggerated for convenience of explanation, and may be different from the actual ratios.

Figure 2:
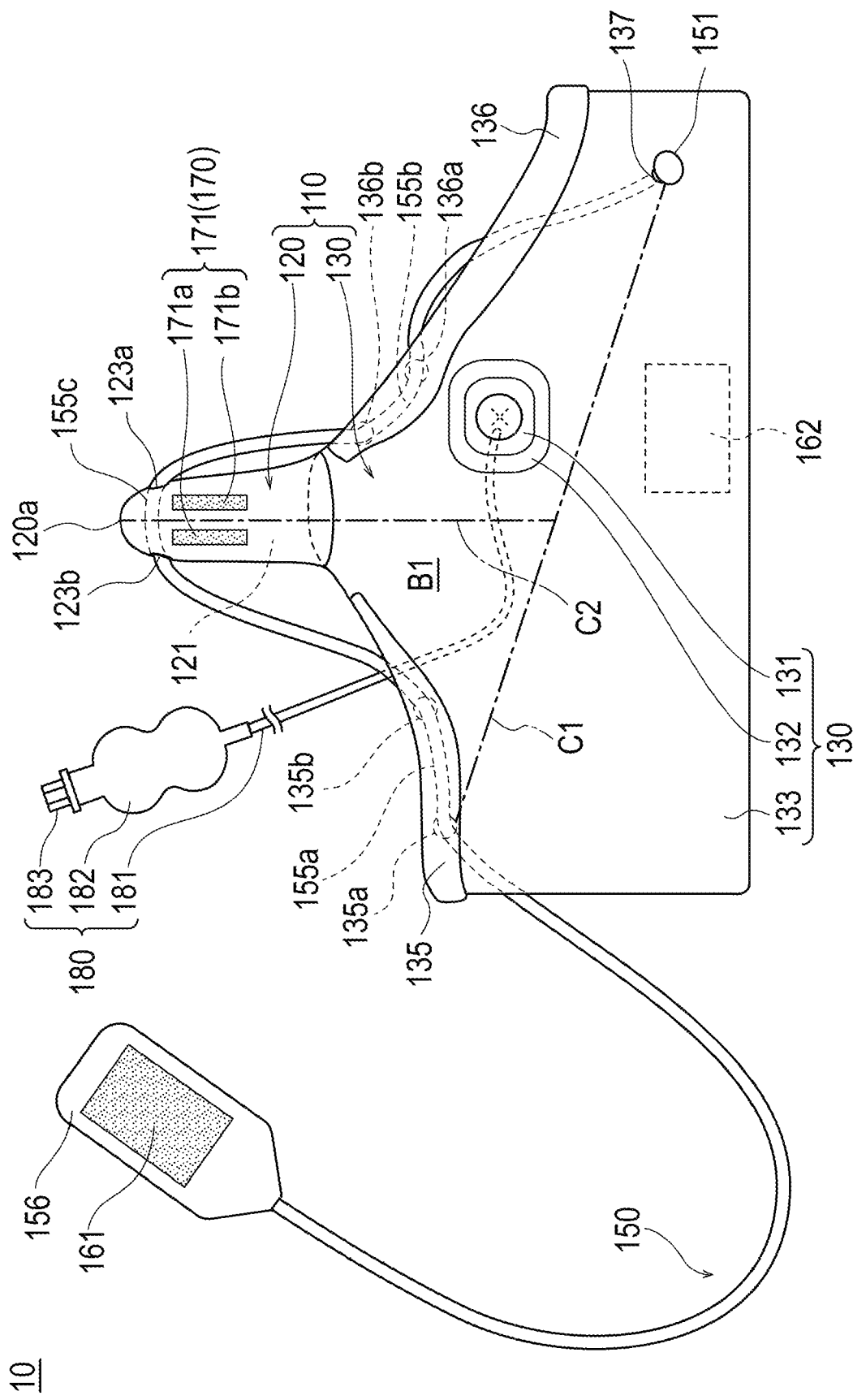
FIG. 2 is a plan view of the hemostatic device according to the embodiment as viewed from an inner surface side of the hemostatic device.

FIGS. 1 and 2 are views illustrating a hemostatic device 10 and FIGS. 3 to 6 are views illustrating a procedure for mounting the hemostatic device 10.

For example, as illustrated in FIGS. 3 to 6, the hemostatic device 10 can be used to support hemostasis on a puncture site t1 after an elongated medical device (for example, introducer) indwelling in the puncture site t1 (corresponding to a "site where bleeding is to be stopped") is removed from the puncture site t1. The puncture site t1 is formed on a radial artery side (for example, a distal radial artery extending around a snuff box or to a fingertip side from the snuff box) of a palmar artery (deep palmar artery) extending to a dorsal side Hb of a hand H of a patient. In the embodiment, an example in which the hemostatic device 10 is used to support hemostasis on the puncture site t1 formed in a left hand of the patient is described, but the hand targeted for use of the hemostatic device 10 may be a right hand.

FIGS. 1 and 2 are plan views of the hemostatic device 10 before the hemostatic device 10 is mounted on the hand H of the patient. In the following description, a mounting surface on a side of a covering member 110 (which is a type of a cover) included in the hemostatic device 10 facing a body surface of the hand H is referred to as an "inner surface" (refer to FIG. 2), and a surface opposite to the inner surface is referred to as an "outer surface" (refer to FIG. 1).

In the following description, a distal side of the covering member 110 is a side located on a fingertip side of a thumb f when the hemostatic device 10 is mounted on the hand H of the patient, and a proximal side of the covering member 110 is a side located on a forearm A side (or wrist side) when the hemostatic device 10 is mounted on the hand H of the patient. In FIGS. 1 and 2, the distal side is a left side in the drawings and the proximal side is a right side in the drawings.

As illustrated in FIGS. 1 and 2, the hemostatic device 10 includes the covering member 110 configured to be worn on the thumb f and hand H of the patient to cover the puncture site t1 on the dorsal side Hb of the hand H of the patient (refer to FIG. 6), a pressing member 140 configured to apply compression force to the puncture site t1 when the covering member 110 covers the puncture site t1, and a linear member 150 configured to secure the covering member 110 to the patient. In the embodiments illustrated herein, the linear member 150 is a string having a predetermined length and a predetermined outer diameter. A specific length and sectional shape of the linear member 150, the material forming the linear member 150, and the like are not limited to any particular length, sectional shape, or material.

As illustrated in FIGS. 1 and 2, the covering member 110 has a first hole portion 135a into which the linear member 150 can be inserted.

As illustrated in FIGS. 1 and 2, the linear member 150 has a connection portion 151 which is connected to the covering member 110. The linear member 150 can form a space 153 into which a portion of the linear member 150 can be inserted between the covering member 110 and the linear member 150 to secure the covering member 110 to the hand H of the patient when the linear member 150 is inserted into the first hole portion 135a.

As illustrated in FIGS. 1 and 2, the pressing member 140 is disposed on the distal side of the covering member 110 from a virtual line C1 passing through the first hole portion 135a and the connection portion 151. Here, as illustrated in FIG. 1, the virtual line C1 is a straight line which connects the first hole portion 135a and the connection portion 151 to each other when the hemostatic device 10 is not mounted on the hand H of the patient and the covering member 110 is spread out. In FIGS. 1 and 2, a virtual line which extends substantially perpendicularly from a tip 120a of the covering member 110 to a proximal side of the hemostatic device 10 and divides the virtual line C1 into two when the hemostatic device 10 is not mounted on the hand H of the patient and the covering member 110 is spread out, is indicated by a reference sign C2.

The hemostatic device 10 may be configured so that at least a portion of the pressing member 140 is disposed on the distal side of the covering member 110 from the virtual line C1 passing through the first hole portion 135a and the connection portion 151 to cause the pressing member 140 to come into close contact with the hand H of the patient. Accordingly, as illustrated in FIG. 1, the "pressing member 140 being disposed on the distal side of the covering member 110 from the virtual line C1 passing through the first hole portion 135a and the connection portion 151" may mean that one half or more of a surface area of the pressing member is disposed on the distal side of the covering member 110 from the virtual line C1 passing through the first hole portion 135a and the connection portion 151 when the hemostatic device 10 is not mounted on the hand H of the patient and the covering member 110 is spread out.

Figure 6:
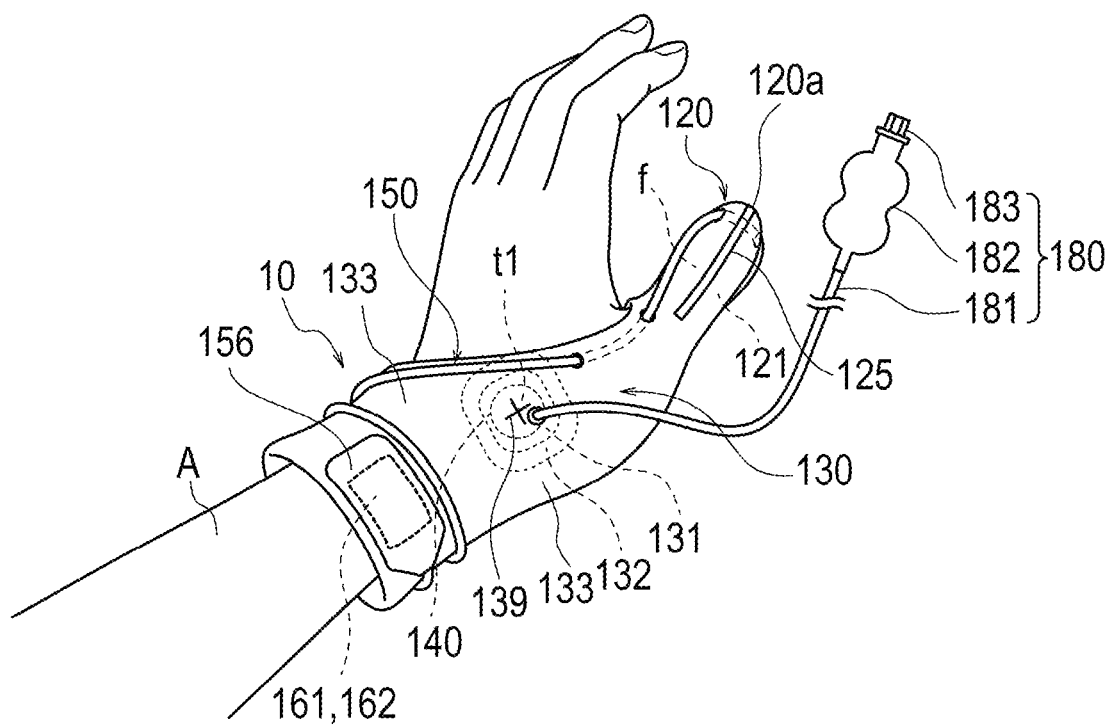

In the hemostatic device 10, the pressing member 140 is disposed in a region B1 which is bounded by the fingertip of the thumb f covered with the covering member 110, the first hole portion 135a, and the connection portion 151 when the hemostatic device 10 is mounted on the patient. As illustrated in FIGS. 1 and 2, the virtual line C1 is a substantially straight line when the hemostatic device 10 is spread out, but the virtual line C1 is arcuate along an outer peripheral surface of the hand H of the patient when the hemostatic device 10 is mounted on the hand H of the patient as illustrated in FIG. 6. In the present embodiment, the pressing member 140 is disposed in the region B1 regardless of whether the virtual line C1 extends linearly or arcuately.

As illustrated in FIG. 1, FIG. 2, and FIG. 6, the covering member 110 includes a finger sack portion 120 configured to be worn on the thumb f of the patient, and a covering portion 130 which is formed on a proximal side of the finger sack portion 120 and configured to cover the dorsal side Hb of the hand H of the patient and the puncture site t1.

The finger sack portion 120 includes a lumen 121 into which the thumb f can be inserted, and a first through hole 123a and a second through hole 123b through which the linear member 150 passes.

The hemostatic device 10 includes one finger sack portion 120 into which the thumb f is inserted. However, for example, in the hemostatic device 10, the finger sack portion 120 may be configured to accommodate a finger (any one of a little finger, a ring finger, a middle finger, and a forefinger) other than the thumb f for insertion therein, or may be configured to accommodate a plurality of fingers for insertion therein. Moreover, the hemostatic device 10 may include a plurality of finger sack portions into which any one finger or a plurality of fingers can be inserted.

As illustrated in FIG. 2, the finger sack portion 120 includes a cavity adjusting mechanism 170 which can adjust a size of the lumen 121 of the finger sack portion 120.

The cavity adjusting mechanism 170 includes a fastener 171 which is disposed on the outer surface of the finger sack portion 120 and can narrow the lumen 121 of the finger sack portion 120. In the present embodiment, the fastener 171 includes a pair of surface fasteners 171a and 171b which is disposed on the outer surface of the finger sack portion 120. For example, the surface fastener 171a can be configured as a female side (or male side) of the surface fastener, and for example, the surface fastener 171b can be configured as a male side (or female side) of the surface fastener. The surface fastener 171a and the surface fastener 171b are secured to each other to be facing each other, and thus, the cavity adjusting mechanism 170 can adjust the lumen 121 of the finger sack portion 120 to be narrowed. Moreover, the securing between the surface fastener 171a and the surface fastener 171b can be released, and as a result, the cavity adjusting mechanism 170 can adjust the lumen 121 of the finger sack portion 120 to be widened. A specific configuration of the fastener 171 is not limited to any particular configuration as long as the fastener 171 can maintain a narrowed state of the lumen 121 of the finger sack portion 120, and may be a belt-shaped fixing member (e.g., securing band) or the like.

As illustrated in FIG. 1, the finger sack portion 120 has a guide marker 125 which provides a guide for maintaining a positional relationship between the finger sack portion 120 and the pressing member 140 when the covering member 110 is mounted on the hand H of the patient.

The guide marker 125 extends substantially linearly along an extending direction of the finger sack portion 120 from the tip 120a of the finger sack portion 120 when the hemostatic device 10 is not mounted to the hand H of the patient. As illustrated in FIG. 1, the guide marker 125 is formed on an outer surface side of the finger sack portion 120. An operator such as a doctor confirms the shape of the guide marker 125 when the hemostatic device 10 is mounted on the hand H of the patient (refer to FIGS. 5 and 6). For example, when the guide marker 125 is twisted while the finger sack portion 120 is worn on the thumb f of the patient, the operator can confirm that the finger sack portion 120 is twisted with respect to the thumb f. If the finger sack portion 120 is twisted with respect to the thumb f, when the covering member 110 is mounted on the hand H of the patient, it is difficult to correctly position the pressing member 140 attached to the covering member 110 at the puncture site t1. Accordingly, in a case where the guide marker 125 is twisted, the operator adjusts the shape of the finger sack portion 120 so that the guide marker 125 has a substantially linear shape, and as a result, the finger sack portion 120 can be properly worn on the thumb f.

As illustrated in FIG. 1, the guide marker 125 is disposed so that an extension line along which the guide marker 125 extends to the proximal side does not overlap the pressing member 140 when the hemostatic device 10 is not mounted on the hand.

A color, a thickness, and a design (for example, a continuous straight line, a broken line, or the like) of the guide marker 125 are not limited to any particular color, thickness, and design, and may be of any color, thickness, and design.

As illustrated in FIGS. 1 and 2, the covering portion 130 includes a first region 131, a second region 132 which is disposed around the first region 131 and is formed of a member having elasticity higher than a material forming the first region 131, and a third region 133 which is disposed around the second region 132 and is formed of a material having elasticity lower than a material forming the second region 132.

The third region 133 of the covering portion 130 is a portion that has the largest area of the covering portion 130 and constitutes a main body portion of the covering portion 130. As illustrated in FIG. 6, when the hemostatic device 10 is mounted on the hand H of the patient, the third region 133 covers a portion of the dorsal side Hb of the hand H of the patient, a portion of a palm of the hand H of the patient, a wrist of the patient, and a portion of the forearm. A of the patient.

The third region 133 of the covering portion 130 has a first insertion portion 135 and a second insertion portion 136 through which the linear member 150 is inserted. The first insertion portion 135 and the second insertion portion 136 are formed on the inner surface side of the covering portion 130 (refer to FIG. 2).

Moreover, the third region 133 of the covering portion 130 has the first hole portion 135a and a second hole portion 135b which communicate with the first insertion portion 135 from the outer surface side of the covering member 110, a third hole portion 136a and a fourth hole portion 136b which communicate with the second insertion portion 136 from an outer surface side of the covering member 110, and a connection hole portion 137 which connects the linear member 150 to the covering portion 130.

As illustrated in FIGS. 1 and 2, the first insertion portion 135 is formed on the inner surface side of the covering portion 130. The first insertion portion 135 has a space into which a portion 155a of the linear member 150 is inserted. In addition, the second insertion portion 136 is formed on the inner surface side of the covering portion 130. The second insertion portion 136 has a space into which a portion 155b of the linear member 150 is inserted.

As illustrated in FIGS. 1 and 2, the first insertion portion 135 and the second insertion portion 136 are disposed in the vicinity of each end portion of the covering member 110 in a width direction (a right-left direction in FIGS. 1 and 2) when the covering member 110 is spread out. A position, a shape, a size, or the like of each of the insertion portions 135 and 136 is not limited to a particular position, shape, or size. A position, a shape, a size, or the like of each of the hole portions 135a, 135b, 136a, and 136b is also not limited to a particular position, shape, or size.

The pressing member 140 is, for example, a balloon which can be inflated and deflated. An injection portion 180 for inflating or deflating the pressing member 140 is connected to the pressing member 140.

The injection portion 180 includes a tube 181 which communicates with an internal space (not illustrated) of the pressing member 140 and has flexibility, a bag body 182 which is disposed at one end portion of the tube 181 to communicate with a lumen of the tube 181, and a tubular connector 183 which houses a check valve (not illustrated) connected to the bag body 182. When the operator or the like inflates the pressing member 140, the operator inserts a tip tube portion of a syringe (not illustrated) into the connector 183 to open the check valve and pushes the plunger of the syringe to inject air in the syringe to the internal space of the pressing member 140. When the pressing member 140 is inflated by the above-described operation, the bag body 182 which communicates with the internal space of the pressing member 140 via the tube 181 is also inflated. By checking the inflation of the bag body 182, the operator can easily check visually that the pressing member 140 can be pressurized without air leakage. A fluid used to inflate the pressing member 140 is not limited to air. When the operator deflates the pressing member 140 (or when the operator decreases the compression force applied by the pressing member 140), the operator connects the syringe to the connector 183. The operator operates the syringe to discharge the air of the internal space of the pressing member 140, and thus, the operator can deflate the pressing member 140.

Moreover, the pressing member 140 is not limited to a balloon as long as the pressing member 140 can apply the compression force to the puncture site t1. For example, it is possible to use as the pressing member 140, a mechanical member which can vary the amount of pushing on the hand H using an external operation such as rotation, a member that includes a plastic resin material or gel for pushing the hand H so as to provide a surface pressure, a member including hydrophilic gel or a wound material (dressing material) to be brought into contact with the puncture site t1, a member including gel which gradually reduces the compression force by decreasing water content with the lapse of time, an elastic material such as sponge-like substances, aggregates of fibers such as cotton (or some padding material), metal, a member having a predetermined three-dimensional shape (spherical, ellipsoidal, or triangular pyramid shape), or a member obtained by appropriately combining these materials with each other.

The pressing member 140 is disposed at a position (a position where a portion of the pressing member 140 or the entire pressing member 140 overlaps the first region 131 in the plan views illustrated in FIGS. 1 and 2) corresponding to the first region 131 of the covering portion 130. In addition, the pressing member 140 is arranged on the inner surface side of the first region 131 facing the hand H of the patient when the hemostatic device 10 is mounted on the hand H of the patient (refer to FIG. 2). The pressing member 140 can be secured to the inner surface of the first region 131 by a known method such as adhesion or fusion.

The first region 131 has a marker portion 139 for positioning the pressing member 140 so that the pressing member 140 overlaps the puncture site t1 when the hemostatic device 10 is mounted on the hand H of the patient. The marker portion 139 is disposed at a substantially central position of the pressing member 140 in a plan view.

A shape and color of the marker portion 139, a method for forming the marker portion 139 in the first region 131, or the like is not limited to any particular shape, color, or method. Preferably, portions of the pressing member 140 and the first region 131 overlapping the marker portion 139 in a plan view and peripheries of the portions are translucent or colored and transparent. Accordingly, the operator can visually recognize the puncture site t1 from the outer surface side of the marker portion 139 even when the marker portion 139 overlaps the puncture site t1.

The second region 132 is disposed to surround a periphery of the first region 131. A range (area in a plan view) or a shape in which the first region 131 is formed on the covering portion 130, a range (area in a plan view) or a shape in which the second region 132 is formed on the covering portion 130, or the like is not limited to the illustrated range or shape. Moreover, a shape, a size, or the like of the third region 133 is not limited to a particular shape or size.

For example, the pressing member 140 can be formed of polyolefin such as polyvinyl chloride, polyethylene, polypropylene, polybutadiene, and ethylene-vinyl acetate copolymer (EVA), polyester such as polyethylene terephthalate (PET) and polybutylene terephthalate (PBT), various thermoplastic elastomers such as polyvinylidene chloride, silicone, polyurethane, polyamide elastomer, polyurethane elastomer, and polyester elastomer, or any optional combination thereof (blend resin, polymer alloy, laminate, or the like).

Moreover, for example, the first region 131 of the covering portion 130 can be formed of an acrylic resin, polyvinyl chloride (particularly, hard vinyl chloride), polyolefin such as polyethylene, polypropylene and polybutadiene, polyester such as polyethylene terephthalate (PET) and polybutylene terephthalate (PBT), polystyrene, poly-(4-methylpentene-1), polycarbonate, an ABS resin, polymethylmethacrylate, polyacetal, polyacrylate, polyacrylonitrile, ionomer, acrylonitrile-butadiene-styrene copolymer, polyvinylidene fluoride, a fluorine-based resin such as polytetrafluoroethylene, a butadiene-styrene copolymer, an aromatic or aliphatic polyamide, or the like. Preferably, the first region 131 is formed of a material having elasticity lower than those of the second region 132 and the third region 133. Moreover, it is preferable that the first region 131 is substantially transparent. Accordingly, the operator can visually recognize the puncture site t1 of the patient through the first region 131 from the outside.

In addition, for example, the second region 132 of the covering portion 130 can be formed of the same material as that of the pressing member 140, that is, polyolefin such as polyvinyl chloride, polyethylene, polypropylene, polybutadiene, and ethylene-vinyl acetate copolymer (EVA), polyester such as polyethylene terephthalate (PET) and polybutylene terephthalate (PBT), various thermoplastic elastomers such as polyvinylidene chloride, silicone, polyurethane, polyamide elastomer, polyurethane elastomer, and polyester elastomer, or any optional combination thereof (blend resin, polymer alloy, laminate, or the like). Preferably, the second region 132 is formed of a material having elasticity higher than those of the first region 131 and the third region 133.

Moreover, for example, the third region 133 of the covering portion 130 can be formed of the same material as that of the pressing member 140, that is, polyolefin such as polyvinyl chloride, polyethylene, polypropylene, polybutadiene, and ethylene-vinyl acetate copolymer (EVA), polyester such as polyethylene terephthalate (PET) and polybutylene terephthalate (PBT), various thermoplastic elastomers such as polyvinylidene chloride, silicone, polyurethane, polyamide elastomer, polyurethane elastomer, and polyester elastomer, or any optional combination thereof (blend resin, polymer alloy, laminate, or the like). For example, the material of the third region 133 may be formed by producing fibers from polyethylene terephthalate (PET) and weaving the fibers. Preferably, the third region 133 is formed of a material having elasticity higher than that of the first region 131 and lower than that of the second region 132. Moreover, the material of third region 133 is not limited to the resin material and may use a paper material or a leather material. In one embodiment, the finger sack portion 120 can be formed integrally with the third region 133 using the same material as that of the third region 133 of the covering portion 130.

Moreover, preferably, in the present embodiment, the first region 131 is formed of a material having elasticity lower than those of the second region 132 and the third region 133. Moreover, preferably, the second region 132 is formed of a material having elasticity higher than that of the third region 133. As an example of a combination of the above-described materials, the first region 131 is formed of a hard vinyl chloride material, the second region 132 is formed of a polyurethane material, and the third region 133 is formed of a soft vinyl chloride material or a material produced by weaving PET fibers. In addition, preferably, the first region 131 is formed of a material which is harder than those of the second region 132 and the third region 133. The first region 131 may be harder than the second region 132 and the third region 133 by adjusting thicknesses of the second region 132 and the third region 133.

As illustrated in FIG. 2, the connection portion 151 which fixes the linear member 150 to the covering portion 130 is provided on one end portion of the linear member 150. The one end portion of the linear member 150 is inserted from the outer surface side of the covering member 110 into the connection hole portion 137 and is disposed on the inner surface side of the covering member 110.

The one end portion of the linear member 150 extends out from the connection hole portion 137, and the connection portion 151 is configured to prevent disconnection of the linear member 150 from the covering member 110. In the present embodiment, the connection portion 151 includes a locking member having an outer shape larger than the connection hole portion 137. The connection portion 151 is secured to the covering member 110 to prevent disconnection of the linear member 150 from the covering member 110, but it is not fully fixed to the covering member 110, such that it is rotatable with respect to the connection hole portion 137. Therefore, the connection portion 151 can prevent the linear member 150 from detaching from the connection hole portion 137, while also preventing the linear member 150 from twisting, when the linear member 150 is wound around the hand H of the patient according to the shape of the hand H.

An interlock portion 156 for interlocking the linear member 150 to the outer surface of the covering portion 130 when the hemostatic device 10 is mounted on the hand H of the patient is provided on the other end portion of the linear member 150 (an end portion of the linear member 150 opposite to the end portion on which the connection portion 151 is provided). As illustrated in FIG. 2, a first connecting member 161 is disposed on the interlock portion 156. Further, as illustrated in FIG. 1, a second connecting member 162 which can be interlocked to or separated from the first connecting member 161 is disposed on the outer surface of the third region 133 of the covering portion 130. As illustrated in FIG. 6, when the hemostatic device 10 is mounted on the hand H of the patient, the linear member 150 and the third region 133 of the covering portion 130 are interlocked to each other by the first connecting member 161 and the second connecting member 162. For example, the first connecting member 161 can be configured as a female side (or male side) of a surface fastener, and for example, the second connecting member 162 can be configured as a male side (or female side) of the surface fastener. However, the structure of each of the connecting members 161 and 162 is not limited to any particular structure as long as the connecting members have a structure which can be interlocked to or separated from each other.

As illustrated in FIGS. 1 and 2, the connection portion 151 of the linear member 150 is disposed on the inner surface side of the covering member 110 when the hemostatic device 10 is not mounted on the hand H of the patient.

From the one end portion side provided with the connection portion 151, a portion of the linear member 150 having a predetermined length is inserted into the second insertion portion 136. Specifically, as illustrated in FIG. 1, the linear member 150 is inserted into the second insertion portion 136 from the outer surface side of the covering member 110 through the third hole portion 136a. Moreover, the linear member 150 is led out to the outer surface side of the covering member 110 from the second insertion portion 136 through the fourth hole portion 136b.

In the linear member 150, a portion extending between the connection portion 151 of the linear member 150 and the third hole portion 136a forms the space 153 (gap between the outer surface of the covering member 110 and the linear member 150).

A portion of the linear member 150 which is led out to the outside of the second insertion portion 136 through the fourth hole portion 136b is inserted into the lumen 121 of the finger sack portion 120. Specifically, as illustrated in FIG. 1, the linear member 150 is inserted into the lumen 121 of the finger sack portion 120 from the outside of the finger sack portion 120 through the first through hole 123a. Moreover, the linear member 150 is led out from the lumen 121 of the finger sack portion 120 to the outside of the finger sack portion 120 through the second through hole 123b.

A portion of the linear member 150 which is led out from the lumen 121 of the finger sack portion 120 to the outside through the second through hole 123b is inserted into the first insertion portion 135. Specifically, as illustrated in FIG. 1, the linear member 150 is inserted into the first insertion portion 135 from the outer surface side of the covering member 110 through the second hole portion 135b. In addition, the linear member 150 is led out to the outer surface side of the covering member 110 from the first insertion portion 135 through the first hole portion 135a. The interlock portion 156 which is disposed on the other end portion of the linear member 150 prevents the other end portion of the linear member 150 from accidentally passing through the hole portions 135a and 135b.

Next, an example of using the hemostatic device 10 will be described with reference to FIGS. 3 to 6. Hereinafter, a procedure of mounting the hemostatic device 10 on the hand H of the patient will be primarily described.

Figure 3:
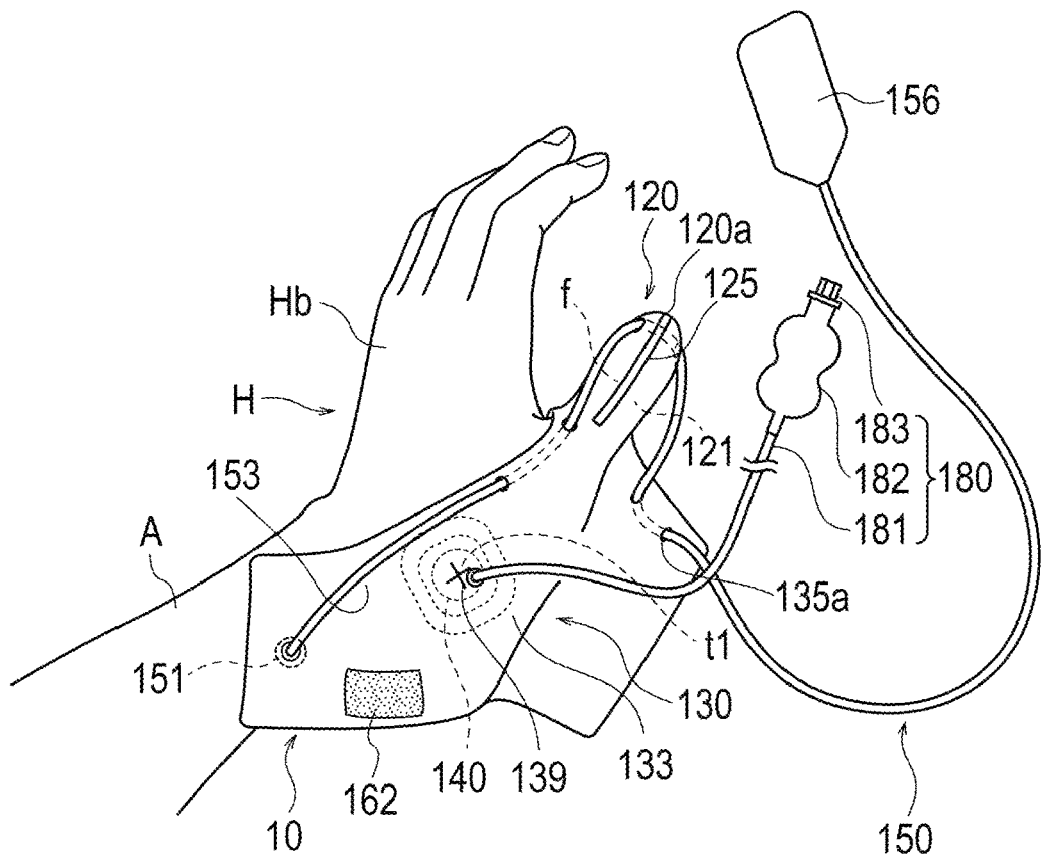
FIGS. 3-6 are perspective views illustrating different states of mounting the hemostatic device according to the embodiment on a hand of a patient.

FIG. 3 illustrates a state when the medical device such as the introducer is inserted into the distal radial artery via the puncture site t1 formed on the dorsal side Hb of the hand H of the patient and various procedures are performed, and thereafter, the hemostasis of the puncture site t1 starts. The medical device is not illustrated in FIGS. 3 to 6.

First, as illustrated in FIG. 3, the operator such as a doctor inserts the thumb f of the patient into the lumen 121 of the finger sack portion 120. Moreover, the operator places the covering member 110 on the hand H and the forearm A of the patient so as to cover the dorsal side Hb of the hand H with the covering portion 130. The operator places the marker portion 139 around the puncture site t1 while checking the positions of the marker portion 139 and the puncture site t1. Further, the operator positions the guide marker 125 so that the guide marker 125 is located at a center of the thumb f. Accordingly, when the operator disposes the marker portion 139 around the puncture site t1, the operator can check whether the finger sack portion 120 is twisted with respect to the thumb f.

Figure 4:
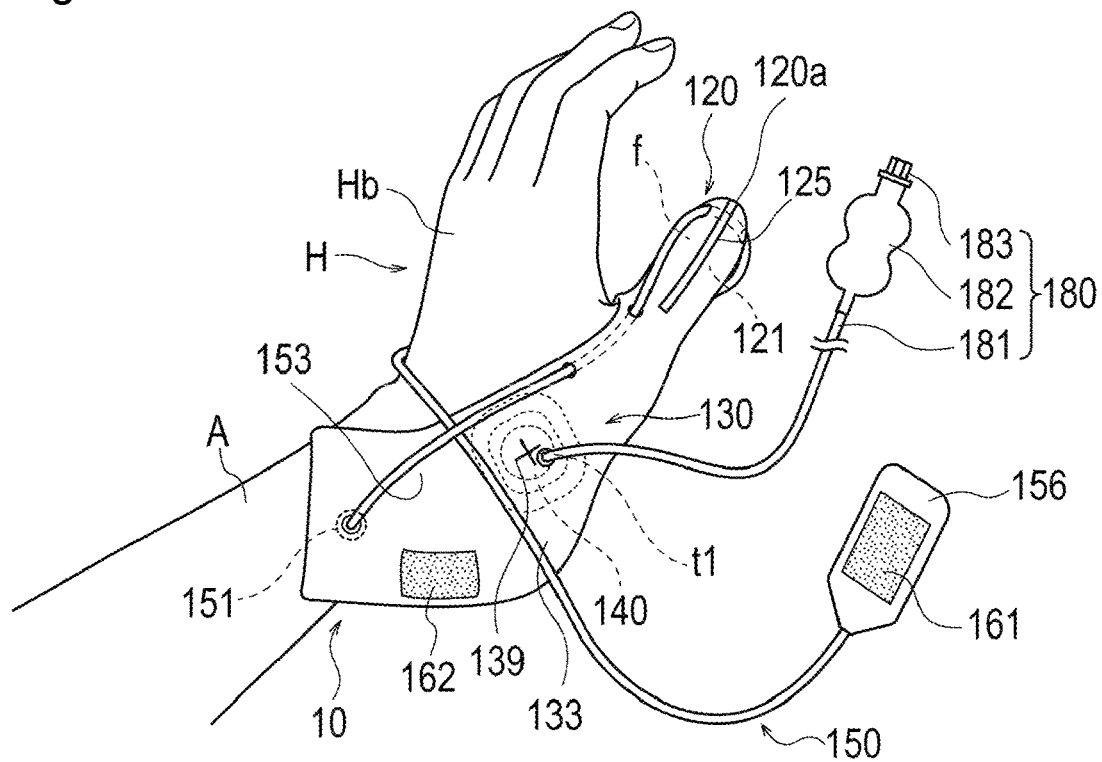

Next, as illustrated in FIG. 4, the operator causes the other end portion side on which the interlock portion 156 of the linear member 150 is disposed to pass through the space 153 formed between the linear member 150 and the covering member 110. Then, the operator maneuvers the linear member 150 so that the linear member 150 is wound counterclockwise in a circumferential direction of the hand H of the patient.

Figure 5:
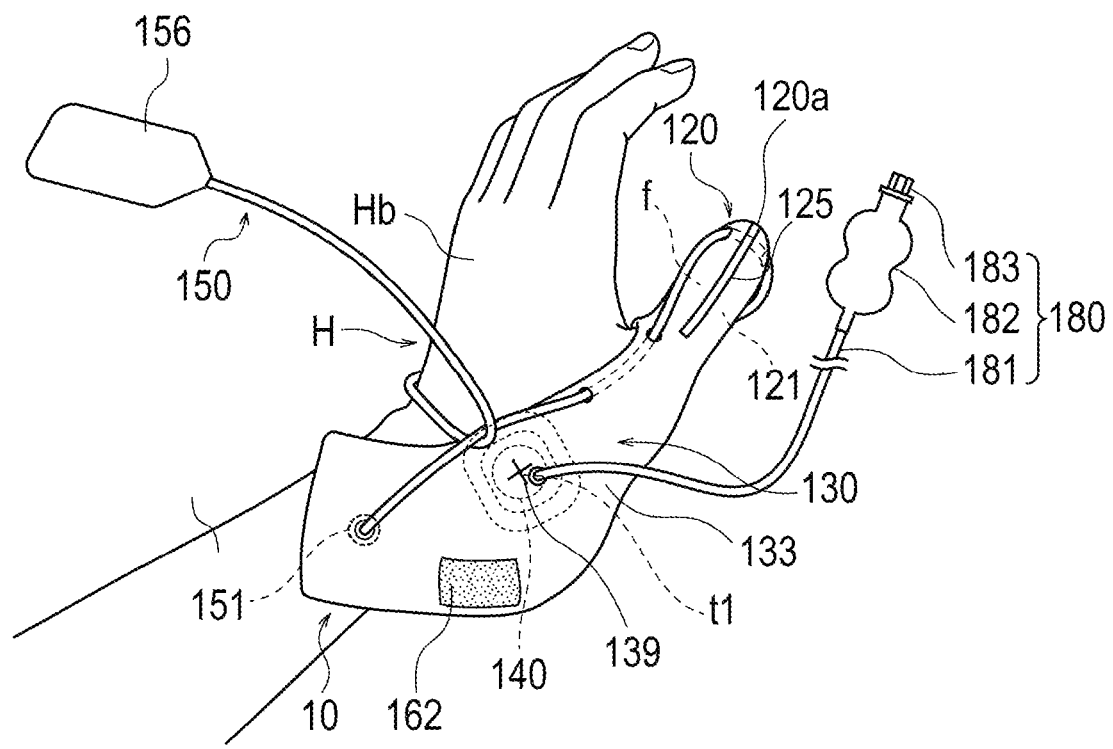

Next, as illustrated in FIG. 5, the operator folds back the linear member 150 so that a portion of the linear member 150 is hooked on the portion forming the space 153. Then, the operator maneuvers the linear member 150 so that the linear member 150 is wound clockwise in the circumferential direction of the hand H of the patient.

Next, as illustrated in FIG. 6, the operator interlocks the first connecting member 161 disposed on the one end portion of the linear member 150 with the second connecting member 162 disposed on the covering portion 130. The operator checks the positions of the puncture site t1 and the marker portion 139 before interlocking the first connecting member 161 and the second connecting member 162 to each other, and thus, can accurately position the pressing member 140 at the puncture site t1.

Next, the operator inflates the pressing member 140 using the injection portion 180 and the syringe (not illustrated). The pressing member 140 is inflated, and thus, the pressing member 140 applies the compression force to the puncture site t1. The operator removes the medical device such as the introducer from the puncture site t1 while the operator maintains the state in which the pressing member 140 applies the compression force to the puncture site t1.

Effects of the hemostatic device 10 according to the present embodiment will be described.

The hemostatic device 10 according to the present embodiment includes the covering member 110 configured to be worn on the thumb f of the patient and to cover the puncture site t1 on the dorsal side Hb of the hand H of the patient, the pressing member 140 configured to apply compression force to the puncture site t1 when the covering member 110 covers the puncture site t1, and the linear member 150 configured to secure the covering member 110 to the hand. The covering member 110 has the first hole portion 135a into which the linear member 150 has been inserted. The linear member 150 has the connection portion 151 which is connected to the covering member 110, and the linear member 150 can form the space 153 into which a portion of the linear member 150 can be inserted between the covering member 110 and the linear member 150 to secure the covering member 110 to the hand H of the patient after the linear member 150 has been inserted into the first hole portion 135a. The pressing member 140 is disposed on the distal side of the covering member 110 relative to the virtual line C1 passing through the first hole portion 135a and the connection portion 151.

In the hemostatic device 10 having the above-described configuration, a force for securing the covering member 110 to the hand H acts on the first hole portion 135a side and the connection portion 151 side with the fingertip of the thumb f as a base point when the pressing member 140 applies the compression force to the puncture site t1. Accordingly, the pressing member 140 can be in close contact with the hand H of the patient. Moreover, in the hemostatic device 10, the covering member 110 is mounted on the thumb f of the hand H of the patient. Accordingly, a predetermined range of the hand H including the puncture site t1 with the thumb f as the base point is covered and the puncture site t1 can be pressed. Therefore, the hemostatic device 10 can be used in various patients regardless of a size of the hand H which may differ from patient to patient.

Moreover, in the hemostatic device 10, the linear member 150 is wound along the circumferential direction of the hand H of the patient, and thus, the covering member 110 disposed between the hand H of the patient and the linear member 150 is secured to the hand H of the patient. Accordingly, in the hemostatic device 10, the entire covering member 110 is not secured to the hand H of the patient when the hemostatic device 10 is mounted on the hand H of the patient. Therefore, when the patient moves the hand H, the hemostatic device 10 can prevent a force which restricts the movement of the hand H of the patient from being applied to the hand H of the patient. As a result, the hemostatic device 10 allows for a high degree of freedom in the movement of the hand H of the patient even while the hemostasis is supported by the hemostatic device 10.

Moreover, the covering member 110 includes the finger sack portion 120 configured to be worn on the thumb f of the patient and the covering portion 130 which is formed on the proximal side of the finger sack portion 120 and configured to cover the dorsal side Hb and the puncture site t1 of the hand H of the patient. The covering portion 130 has the first region 131, the second region 132 which is disposed around the first region 131 and is formed of the member having elasticity higher than that of the material forming the first region 131, and the third region 133 which is disposed around the second region 132 and is formed of the material having elasticity lower than the material forming the second region 132. The pressing member 140 is disposed at a position corresponding to the first region 131.

In the hemostatic device 10 having the above-described configuration, the finger sack portion 120 is worn on the thumb f of the patient, and thus, the covering member 110 can be easily mounted on the thumb f. Moreover, the elasticity of the first region 131 of the covering portion 130 is lower than that of the second region 132, and thus, it is possible to prevent a compression force applied to the puncture site t1 by the pressing member 140 from being dispersed. In addition, the elasticity of the second region 132 of the covering portion 130 is higher than the elasticity of the first region 131. Accordingly, the second region 132 is in close contact with the hand H around the first region 131, and it is possible to prevent the pressing member 140 from being displaced from the puncture site t1. Moreover, the elasticity of the third region 133 of the covering portion 130 is lower than that of the second region 132. Accordingly, it is possible to prevent the third region 133 from being unintentionally expanded and contracted in the state where the hemostatic device 10 is mounted on the hand H of the patient. Therefore, the hemostatic device 10 can prevent the mounting position of the hemostatic device 10 from being displaced.

Moreover, the material forming the first region 131 of the covering portion 130 has elasticity lower than that of the material forming the third region 133 of the covering portion 130 and is harder than those of the second region 132 and the third region 133. Moreover, in the hemostatic device 10, it is possible to more effectively maintain the pressing member 140 at the position corresponding to the first region 131 while the pressing member 140 presses against the puncture site t1, and thus, hemostatic effects can be enhanced.

Moreover, the finger sack portion 120 includes the cavity adjusting mechanism 170 which can adjust the size of the lumen 121 of the finger sack portion 120. Accordingly, in the hemostatic device 10, it is possible to improve adhesiveness of the finger sack portion 120 to a base or the like of the thumb f by reducing the lumen 121 of the finger sack portion 120. As a result, in the hemostatic device 10, it is possible to prevent the finger sack portion 120 from being displaced.

Moreover, the cavity adjusting mechanism 170 has the fastener 171 which is disposed on the outer surface of the finger sack portion 120 and can narrow the lumen 121 of the finger sack portion 120. Therefore, in the hemostatic device 10, it is possible to easily narrow the lumen 121 of the finger sack portion 120 using the fastener 171.

Moreover, the finger sack portion 120 has the through holes 123a and 123b through which the linear member 150 can pass. Accordingly, in the hemostatic device 10, the linear member 150, which is disposed at the first hole portion 135a, the connection portion 151, and the finger sack portion 120, applies a securing force to the first hole portion 135a side and the connection portion 151 side with the first sack portion 120 side as a base point, when the hemostatic device 10 is mounted on the hand H of the patient. Accordingly, in the hemostatic device 10, it is possible to more stably secure the hemostatic device 10 to the hand H of the patient.

Moreover, the finger sack portion 120 has the guide marker 125 which provides a guide for maintaining the positional relationship between the finger sack portion 120 and the pressing member 140 when the covering member 110 is mounted on the hand H of the patient. Accordingly, in the hemostatic device 10, it is possible to prevent the finger sack portion 120 from being twisted when mounted on the thumb f.

Next, modification examples of the cavity adjusting mechanism for adjusting the size of the lumen 121 of the finger sack portion 120 will be described. In the following descriptions of the modification examples, the same reference signs as those used in the above-described embodiment are assigned to the same elements, and descriptions thereof are not repeated.

Figure 7:
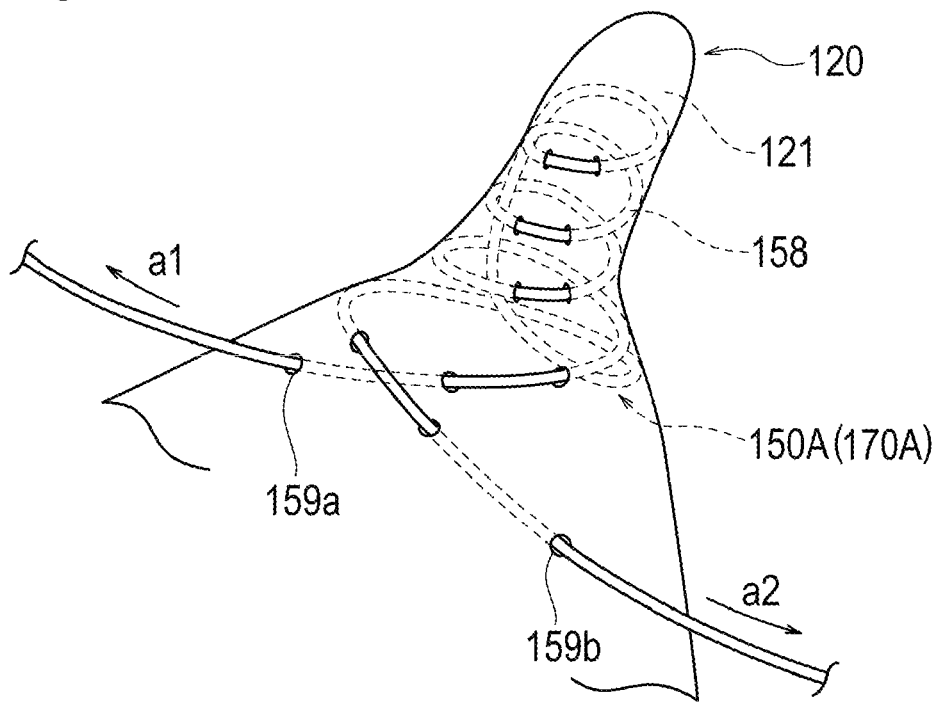
FIG. 7 is a perspective view schematically illustrating a first modified example of a cavity adjusting mechanism included in a finger sack portion of the hemostatic device according to the embodiment.

FIG. 7 illustrates a cavity adjusting mechanism 170A according to the first modification example.

The cavity adjusting mechanism 170A includes a portion of a linear member 150A. Specifically, the linear member 150A has a winding portion 158 which is wound in a predetermined shape on the lumen 121 of the finger sack portion 120 and the outer surface side of the finger sack portion 120.

The linear member 150A is led out to the outer surface side of the covering portion 130 through each of through holes 159a and 159b. In the linear member 150A, a portion of the winding portion 158 extends spirally on the lumen 121 of the finger sack portion 120 and the outer surface of the finger sack portion 120. The operator pulls both end portion sides of the linear member 150A outside the finger sack portion 120 as illustrated by arrows a1 and a2, and thus, can contract the spirally extending portion of the winding portion 158. The winding portion 158 of the linear member 150A is disposed so that a portion of the winding portion 158 is exposed on the outer surface side of the finger sack portion 120. Accordingly, when the linear member 150A is pulled so that the winding portion 158 is contracted, the linear member 150A contracts the finger sack portion 120 from the outer surface side of the finger sack portion 120. Therefore, the finger sack portion 120 becomes deformed so that the lumen 121 of the finger sack portion 120 is narrowed.

Figure 8:
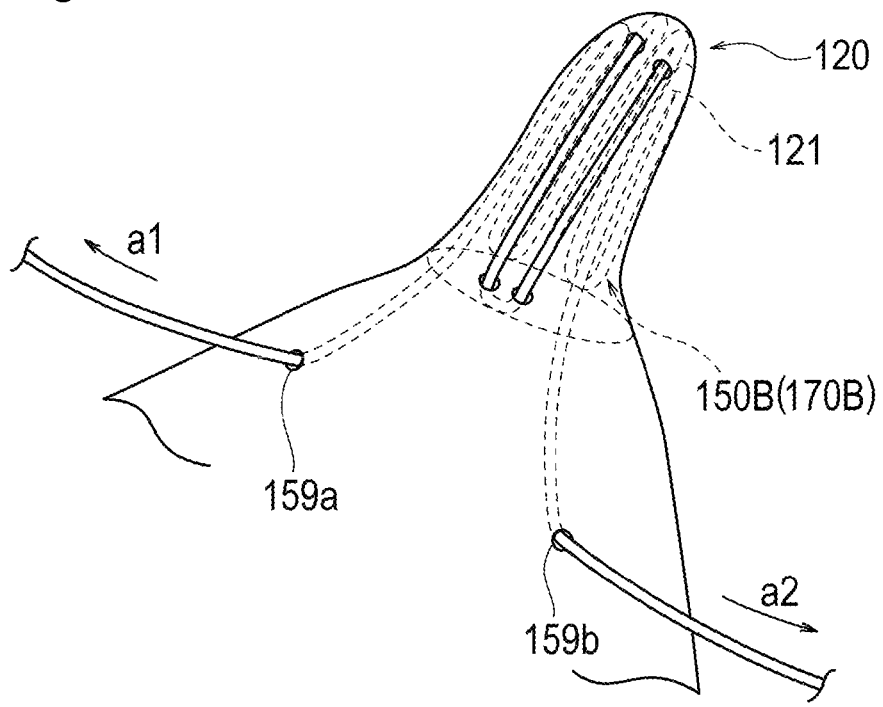
FIG. 8 is a perspective view schematically illustrating a second modified example of the cavity adjusting mechanism included in the finger sack portion of the hemostatic device according to the embodiment.

FIG. 8 illustrates a cavity adjusting mechanism 170B according to a second modification example.

Figure 9:
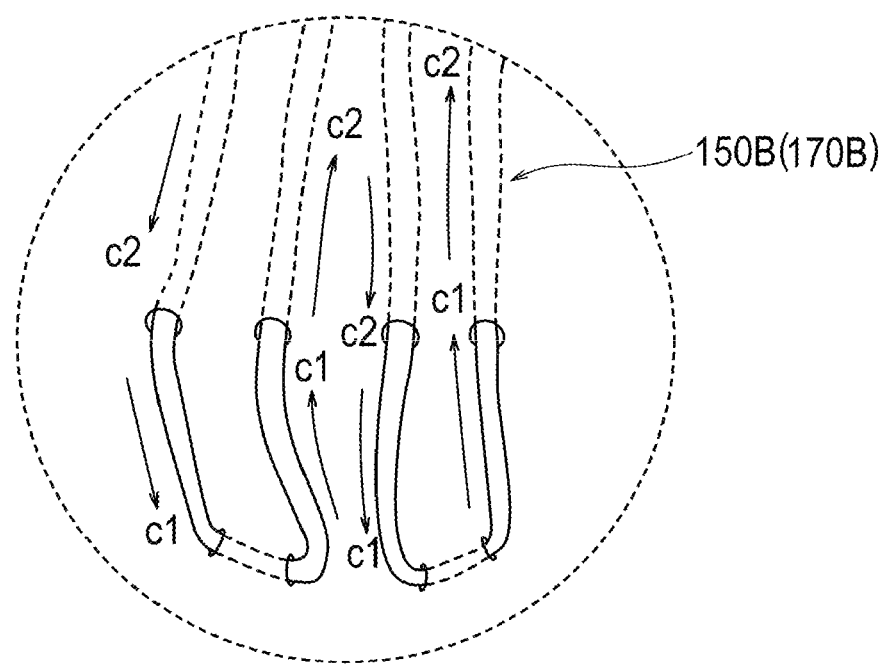
FIG. 9 is a view illustrating an operating principle of the second modified example of the cavity adjusting mechanism included in the finger sack portion of the hemostatic device according to the embodiment.

The cavity adjusting mechanism 170B includes a portion of a linear member 150B. A portion of the linear member 150B is disposed in the lumen 121 of the finger sack portion 120, and a portion of the linear member 150B is led out to the outer surface side of the finger sack portion 120. As illustrated in FIG. 9, the linear member 150B reciprocates along a longitudinal direction (direction of arrow c1) and a depth direction (direction of arrow c2) of the finger sack portion 120. When the operator pulls the linear member 150A as illustrated by the arrows a1 and a2 in FIG. 8 outside the finger sack portion 120, the linear member 150B is pulled to alternately move in the longitudinal direction and the depth direction as illustrated in FIG. 9. Then, in the linear member 150B, a portion (a portion exposed from the finger sack portion 120) disposed near the base portion of the finger sack portion 120 is compressed so as to tighten the finger sack portion 120. Therefore, the operator can easily narrow the lumen 121 of the finger sack portion 120 by pulling the linear member 150B.

Hereinbefore, the hemostatic device according to one or more embodiments has been described. However, the configurations of the embodiments described in the specification are not limiting, and may be appropriately changed based on the language of claims.

For example, in the descriptions of the embodiment, the hemostatic device for supporting hemostasis on the puncture site formed in the left hand is given as an example. However, the hemostatic device can be used for supporting hemostasis on a puncture site formed in the right hand. When the hemostatic device is used in the right hand, the shape of the covering member, the position of the pressing member, or the like can be appropriately changed to support hemostasis on the puncture site formed in the right hand.

What is claimed is:

1. A hemostatic device comprising:
a cover configured to be worn on a hand of a patient to cover a site on a dorsal side of the hand of the patient where bleeding is to be stopped, the cover including a finger cover to be worn on a finger of the hand, the cover having a first hole at the finger cover and a second hole at a first end of the cover;
a pressing member by which the site where the bleeding is to be stopped is compressed when the cover is worn and the pressing member is positioned on the site where the bleeding is to be stopped; and
a string configured to secure the cover to the hand, one end of the string being connected to a second end of the cover opposite to the first end of the cover, the string passing through the first and second holes,
wherein the pressing member is disposed on a distal side of the cover relative to a virtual line passing through a center of the second hole and a center of a connection point of said one end of the string to the second end of the cover, the distal side of the cover being closer to the finger cover than a proximal side thereof.

2. The hemostatic device according to claim 1,
wherein the cover has a first region, a second region which is disposed around the first region and is formed of a material having elasticity higher than that of a material forming the first region, and a third region which is disposed around the second region and is formed of a material having elasticity lower than the material forming the second region, and
wherein the pressing member is located in the first region.

3. The hemostatic device according to claim 2,
wherein the material forming the first region has elasticity lower than that of the material forming the third region and is harder than the materials of the second region and the third region.

4. The hemostatic device according to claim 2,
wherein the finger cover has a lumen, a size of which is adjustable.

5. The hemostatic device according to claim 4,
wherein the finger cover includes a fastener on an outer surface of the finger cover, the fastener having first and second portions which, when attached to each other, narrows the lumen of the finger cover.

6. The hemostatic device according to claim 2,
wherein the finger cover has a guide marker which provides a guide for maintaining a positional relationship between the finger cover and the pressing member when the cover is mounted on the hand of the patient.

7. A hemostatic device to be worn on a hand of a patient, on a dorsal side of which is located a site where bleeding is to be stopped, the hemostatic device comprising:
- a cover including a finger cover configured to be worn on at least one finger of the hand and a body portion configured to be worn around the dorsal side of the hand, the body portion including a first region to be positioned on the site where bleeding is to be stopped, a second region that is more elastic than the first region, surrounding the first region, and a third region that is more elastic than the first region and less elastic than the second region, surrounding the second region;
- a pressing member located in the first region and configured to apply compression force to the site when the cover is secured to the hand of the patient; and
- a string that has been inserted into a plurality of holes of the cover, the string having a first end connected to the cover and a second end that is attached to the cover when the cover is secured to the hand of the patient and detached from the cover to allow the cover to be removed from the hand of the patient,
- wherein the pressing member is disposed on a distal side of the cover relative to a virtual line passing through one of the holes and a connection point of the first end of the string to the cover.

8. The hemostatic device according to claim 7, wherein the string passes through the holes at various locations along the length of the string including a first location along the length of the string that is closest to the first end and a second location along the length of the string that is closest to the second end, and
the virtual line passes through one of the holes, which surrounds the string at the second location.

9. The hemostatic device according to claim 8,
wherein two of the holes are formed on the finger cover and two of the holes, including the hole that surrounds the string at the first location, are formed on the body portion between the finger cover and the connection point of the first end of the string to the cover.

10. The hemostatic device according to claim 9, wherein the body portion includes a palmar portion that is configured to cover the palmar portion of the hand of the patient when the cover is secured to the hand of the patient, and
two of the holes, including the hole that surrounds the string at the second location, are formed on the palmar portion.

11. The hemostatic device according to claim 7,
wherein a size of a lumen of the finger cover is adjustable.

12. The hemostatic device according to claim 11,
wherein the finger cover includes a fastener on an outer surface thereof, the fastener having first and second portions which, when attached to each other, narrows the lumen of the finger cover.

13. The hemostatic device according to claim 11,
wherein the finger cover is configured to provide a spiral shaped path to the string that has been inserted into the finger cover, and to decrease the size of the lumen of the finger cover when the second end of the string is pulled away from the connection point of the first end of the string to the cover.

14. The hemostatic device according to claim 11,
wherein the finger cover is configured to provide a path that reciprocates in a longitudinal direction of the finger cover, to the string that has been inserted into the finger cover, and to decrease the size of the lumen of the finger cover when the second end of the string is pulled away from the connection point of the first end of the string to the cover.

15. The hemostatic device according to claim 11,
wherein the finger cover has a guide marker which provides a guide for maintaining a positional relationship between the finger cover and the pressing member when the cover is secured to the hand of the patient.

16. The hemostatic device according to claim 7,
wherein the first region and the pressing member are transparent and the first region has a marker at a location corresponding to the pressing member.

17. The hemostatic device according to claim 7,
wherein the pressing member is inflatable and is inflated to apply the compression force to the site.

18. A method of treating a puncture site located on a dorsal side of a hand of a patient for hemostasis, said method comprising:
- mounting a cover of a hemostatic device on the hand, the cover including a finger cover into which at least one finger of the hand is inserted and a body portion that covers the dorsal side of the hand, the cover having a first hole at the finger cover and a second hole at a first end of the cover;
- positioning a pressing member of the hemostatic device on the puncture site; and
- pulling on one end of a string that is connected to a second end of the cover opposite to the first end of the cover and fed through the first and second holes and attaching said one end of the string to the cover to secure the cover to the hand, wherein
- the pressing member is disposed on a distal side of the cover relative to a virtual line passing through a center of the second hole and a center of a connection point of the other end of the string to the second end of the cover, the distal side of the cover being closer to the finger cover than a proximal side thereof.

19. The method according to claim 18, further comprising:
- inflating the pressing member to apply a compression force to the puncture site.

* * * * *